United States Patent [19]

Stemp et al.

[11] Patent Number: 5,147,866

[45] Date of Patent: Sep. 15, 1992

[54] 1,2-DIAMINO-CYCLOBUTEN-3,4-DIONE DERIVATIVES

[75] Inventors: Geoffrey Stemp, Harlow; Gordon Burrell, Ulverston, both of England

[73] Assignee: Beecham Group p.l.c., England

[21] Appl. No.: 604,874

[22] Filed: Oct. 29, 1990

[30] Foreign Application Priority Data

Oct. 30, 1989 [GB] United Kingdom ............... 8924373

[51] Int. Cl.$^5$ ................ A61K 31/665; A61K 31/35; C07D 311/22; C07D 311/04
[52] U.S. Cl. ................... 514/100; 514/456; 549/218; 549/345; 549/399
[58] Field of Search ............... 514/456, 100; 549/399, 549/218, 345

[56] References Cited

U.S. PATENT DOCUMENTS

| | | | |
|---|---|---|---|
| 4,363,811 | 12/1982 | Evans et al. | 549/399 |
| 4,366,163 | 12/1982 | Evans et al. | 549/399 |
| 4,391,815 | 7/1983 | Evans | 549/399 |
| 4,446,113 | 5/1984 | Evans et al. | 549/399 |
| 4,496,565 | 1/1985 | Evans et al. | 514/228.2 |
| 4,542,149 | 9/1985 | Evans et al. | 514/278 |
| 4,687,779 | 8/1987 | Evans | 514/456 |
| 4,782,083 | 11/1988 | Cassidy et al. | 514/456 |
| 4,800,212 | 1/1989 | Evans et al. | 514/424 |
| 4,812,459 | 3/1989 | Evans et al. | 514/241 |
| 4,925,839 | 5/1990 | Quagliato et al. | 514/456 |

FOREIGN PATENT DOCUMENTS

| | | |
|---|---|---|
| 0250077 | 12/1987 | European Pat. Off. |
| 0277611 | 1/1988 | European Pat. Off. |
| 0277612 | 1/1988 | European Pat. Off. |
| 0314446 | 5/1989 | European Pat. Off. |
| 0321175 | 6/1989 | European Pat. Off. |
| 0363883 | 10/1989 | European Pat. Off. |
| 0339562 | 11/1989 | European Pat. Off. |
| 2523281 | 12/1975 | Fed. Rep. of Germany |
| 8602550 | 5/1986 | PCT Int'l Appl. |
| 8907103 | 8/1989 | PCT Int'l Appl. |
| 2204868 | 11/1988 | United Kingdom |

*Primary Examiner*—C. Warren Ivy
*Assistant Examiner*—Amelia A. Owens
*Attorney, Agent, or Firm*—Rosenman & Colin

[57] ABSTRACT

A compound of formula (I) or a pharmaceutically acceptable salt thereof:

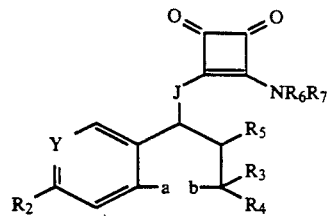

wherein
a and b together form an —O— or —CH$_2$— linkage or a bond;
either Y is N and R$_2$ is hydrogen; or
Y is C-R$_1$
wherein
either one of R$_1$ and R$_2$ is hydrogen and the other is nitro, cyano, halo, —CF$_3$, C$_2$F$_5$, formyl aldoxime, CF$_3$O, NO$_2$—CH=CH—, NC—CH=CH—; a group R$_x$X— wherein R$_x$ is C$_{1-6}$ alkyl, aryl or heteroaryl either of which may be optionally substituted by one, two or three of C$_{1-4}$ alkyl, C$_{1-4}$ alkoxy, nitro, halo, CF$_3$ and cyano; and X is C=O, O.C=O, C=O.O, CHOH, SO, SO$_2$, O.SO, O.SO$_2$, CONH, O.CONH, C=S, O.C=S, C=S.O, CH.SH, SONH, SO$_2$NH, O.SONH, O.SO$_2$NH, CO—CH=CH, C=NHOH, C=NNH$_2$; or a group R$_y$R$_z$NZ— wherein R$_y$ and R$_z$ are independently hydrogen or C$_{1-6}$ alkyl and Z is C=O, SO or SO$_2$; or a group (R$_w$O)$_2$P(O)W wherein R$_w$ is hydrogen or C$_{1-6}$ alkyl and W is O or a bond; or
R$_1$ is a C$_{3-8}$ cycloalkyl group or a C$_{1-6}$ alkyl group optionally substituted by a group R$_9$ which is hydroxy, C$_{1-6}$ alkoxy, amino optionally substituted by one or two C$_{1-6}$ alkyl groups, C$_{1-7}$ alkanoylamino, C$_{3-8}$ cycloalkyloxy or C$_{3-8}$ cycloalkylamino and R$_2$ is hydrogen; or
one of R$_1$ and R$_2$ is nitro, cyano or C$_{1-3}$ alkylcarbonyl and the other is a different group selected from nitro, cyano, halo, C$_{1-3}$ alkylcarbonyl, methoxy or amino optionally substituted by one or two C$_{1-6}$ alkyl or by C$_{2-7}$ alkanoyl; or
R$_1$ and R$_2$ together with the carbon atoms, to which they are attached form 2,1,3-oxadiazole or triazole;
either one of R$_3$ and R$_4$ is hydrogen or C$_{1-4}$ alkyl and the other is C$_{1-4}$ alkyl; or
R$_3$ and R$_4$ together are C$_{2-5}$ polymethylene;
R$_5$ is hydrogen, hydroxy, C$_{1-6}$ alkoxy or C$_{1-7}$ acyloxy or ONO$_2$;
R$_6$ and R$_7$ are independently hydrogen, C$_{1-6}$ alkyl; or (when R$_6$ is hydrogen), then R$_7$ is allyl, propargyl or C$_{3-6}$ cycloalkyl;
J is O or NR$_8$ wherein R$_8$ is hydrogen or C$_{1-6}$ alkyl.

10 Claims, No Drawings

1,2-DIAMINO-CYCLOBUTEN-3,4-DIONE DERIVATIVES

This invention relates to novel compounds having pharmacological activity, to a process for their preparation and to their use as pharmaceuticals.

EP-A-76075, 91748, 107423, 139992, 168619, 205292, 214818, 250077 and 321175 (Beecham Group p.l.c.) describe benzopyran, tetrahydronaphthalene, pyranopyridine and indane derivatives having antihypertensive and/or bronchodilator activity.

EP-A-277611 and 277612 (Hoechst Aktiengesellschaft), EP-A-314446 (American Home Products Corporation), WO 89/07103 (Nissan Chemical Industries Limited) and EP-A-363883 (Merck Patent Gesellschaft mit Beschränkter Haftung), describe further classes of benzopyran derivatives.

A novel group of compounds has now been discovered, which compounds have a substituted cyclobutenedione substituent at the 4- (or equivalent) position. These compounds have been found to have blood pressure lowering activity, useful in the treatment of hypertension, and bronchodilator activity, useful in the treatment of respiratory tract disorders. In addition, these compounds are believed to be $K^+$ channel activators which indicates that they are of potential use in the treatment of disorders associated with smooth muscle contraction of the gastro-intestinal tract, respiratory system, uterus or urinary tract including the ureter. Such disorders include irritable bowel syndrome and diverticular disease; reversible airways obstruction including asthma; premature labour; and incontinence, renal cholic and disorders associated with kidney stones. They are also indicated as of potential use in the treatment of cardiovascular disorders other than hypertension, such as congestive heart failure, angina, peripheral vascular disease, cerebral vascular disease, pulmonary hypertension and right heart failure. They may also be of potential use in the treatment of epilepsy and glaucoma.

Accordingly, the present invention provides a compound of formula (I) or a pharmaceutically acceptable salt thereof:

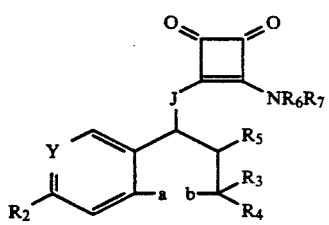

(I)

wherein
a and b together form an —O— or —CH$_2$— linkage or a bond;
either Y is N and R$_2$ is hydrogen; or Y is C-R$_1$
wherein
either one of R$_1$ and R$_2$ is hydrogen and the other is nitro cyano, halo, CF$_3$, C$_2$F$_5$, formyl, aldoxime, CF$_3$O, NO$_2$—CH=CH—, NC—CH=CH—; a group R$_x$X— wherein Rx is C$_{1-6}$ alkyl, aryl or heteroaryl either of which may be optionally substituted by one, two or three of C$_{1-4}$ alkyl, C$_{1-4}$ alkoxy, nitro, halo, CF$_3$ and cyano; and X is C=O, O.C=O, C=O.O, CHOH, SO, SO$_2$, O.SO, O.SO$_2$, CONH, O.CONH, C=S, O.C=S, C=S.O, CH.SH, SONH, SO$_2$NH, O.SONH, O.SO$_2$NH, CO—CH=CH, C=NHOH, C=NNH$_2$; or a group R$_y$R$_z$NZ— wherein R$_y$ and R$_z$ are independently hydrogen or C$_{1-6}$ alkyl and Z is C=O, SO or SO$_2$; or a group (R$_w$O)$_2$P(O)W wherein R$_w$ is hydrogen or C$_{1-6}$ alkyl and W is O or a bond; or R$_1$ is a C$_{3-8}$ cycloalkyl group or a C$_{1-6}$ alkyl group optionally substituted by a group R$_9$ which is hydroxy, C$_{1-6}$ alkoxy, amino optionally substituted by one or two C$_{1-6}$ alkyl groups, C$_{1-7}$ alkanoylamino, C$_{3-8}$ cycloalkyloxy or C$_{3-8}$ cycloalkylamino and R$_2$ is hydrogen; or one of R$_1$ R$_2$ is nitro, cyano or C$_{1-3}$ alkylcarbonyl and the other is a different group selected from nitro, cyano, halo, C$_{1-3}$ alkylcarbonyl, methoxy or amino optionally substituted by one or two C$_{1-6}$ alkyl or by C$_{2-7}$ alkanoyl; or R$_1$ and R$_2$ together with the carbon atoms, to which they are attached form 2,1,3-oxadiazole or triazole;
either one of R$_3$ and R$_4$ is hydrogen or C$_{1-4}$ alkyl and the other is C$_{1-4}$ alkyl; or R$_3$ and R$_4$ together are C$_{2-5}$ polymethylene;
R$_5$ is hydrogen, hydroxy, C$_{1-6}$ alkoxy or C$_{1-7}$ acyloxy or ONO$_2$;
R$_6$ and R$_7$ are independently hydrogen, C$_{1-6}$ alkyl; or (when R$_6$ is hydrogen), then R$_7$ is allyl, propargyl or C$_{3-6}$ cycloalkyl;
J is O or NR$_8$ wherein R$_8$ is hydrogen or C$_{1-6}$ alkyl.

The cyclobutene moiety is cis or trans to the R$_5$ group when R$_5$ is other than hydrogen, preferably trans.

Preferably a and b together form an —O— linkage.

When either one of R$_1$ and R$_2$ is hydrogen, the other is preferably selected from halo, —CF$_3$, C$_2$F$_5$, C$_{1-6}$ alkylcarbonyl, C$_{1-6}$ alkoxycarbonyl, OCF$_3$, nitro or cyano.

When one of R$_1$ and R$_2$ is nitro, cyano or C$_{1-3}$ alkylcarbonyl the other is, favourably, amino optionally substituted by one or two C$_{1-6}$ alkyl groups or by C$_{2-7}$ alkanoyl. In particular, when one of R$_1$ and R$_2$ is nitro, cyano or acetyl, the other is amino, methylamino, dimethylamino or acetylamino. Preferably, when one of R$_1$ and R$_2$ is nitro or cyano, especially cyano, the other is amino.

Halo substituents in R$_1$ and/or R$_2$ are usually chloro or bromo.

Alkyl groups in R$_1$/R$_2$, including R$_x$, R$_y$, R$_z$, R$_w$, are usually selected from methyl, ethyl, n- and iso-propyl, n-, iso-, sec- and tert-butyl. Suitable examples of other alkyl or alkyl containing groups in R$_1$ and in R$_3$ and R$_4$ when alkyl include those listed for R$_x$ alkyl groups. C$_{3-8}$ cycloalkyl includes C$_3$, C$_4$, C$_5$, C$_6$ cycloalkyl, in particular, cyclopentyl.

A sub-group of R$_x$ heteroaryl is 5- or 6-membered monocyclic or 9- or 10-membered bicyclic heteroaryl of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different. Examples of 5- or 6-membered monocyclic heteroaryl containing one, two or three heteroatoms which are selected from the class of oxygen, nitrogen and sulphur include furyl, thienyl, pyrryl, oxazolyl, thiazolyl, imidazolyl and thiadiazolyl, and pyridyl, pyridazyl, pyrimidyl, pyrazyl and triazyl. Preferred examples of such groups include furanyl, thienyl, pyrryl and pyridyl, in particular 2- and 3-furyl, 2- and 3-pyrryl, 2- and 3-thienyl, and 2-, 3- and 4-pyridyl. Examples of 9- or 10-membered bicyclic heteroaryl containing one, two or three heteroatoms which are selected from the class of oxygen, nitrogen and sulphur include benzofuranyl, benzothienyl, indolyl and indazolyl, quinolyl and isoquinolyl, and quinazonyl. Preferred examples of such groups include 2- and 3-benzofuranyl, 2- and 3-benzothienyl, and 2- and 3-indolyl, and 2- and 3-quinolyl.

Preferred examples of the groups or atoms for optional substitution of $R_x$ when aryl or heteroaryl include methyl, methoxy, hydroxy, chloro, nitro or cyano.

$R_1$ is preferably nitro, cyano, acetyl, $CF_3$, $C_2F_5$, $OCF_3$, methyl or ethyl, iso-propyl or cyclopentyl.

Preferably $R_2$ is hydrogen.

Preferably $R_3$ and $R_4$ are both methyl groups.

Suitable examples of $R_5$ when alkoxy include methoxy, ethoxy, n- and iso-propoxy, of which methoxy is preferred. When $R_5$ is $C_{1-7}$ acyloxy it is usually $C_{1-7}$ carboxylic acyloxy, such as $C_{1-7}$ alkanoyloxy wherein the alkyl moiety is usually as listed for alkyl in $R_1$ and $R_2$ above.

$R_5$ is favourably hydroxy or hydrogen, preferably hydroxy.

Suitable values for $R_6$, $R_7$ and $R_8$ when $C_{1-6}$ alkyl or $C_{3-8}$ cycloalkyl include those listed hereinbefore for $R_1$ and/or $R_x$ when $C_{1-6}$ alkyl/$C_{3-8}$ cycloalkyl.

$R_6$ and $R_7$ are preferably hydrogen.

$R_8$ is preferably hydrogen, methyl, ethyl or n-propyl.

Examples of pharmaceutically acceptable salts include acid addition salts with acids such as hydrochloric, hydrobromic, phosphoric, sulphuric, citric, tartaric, lactic or acetic acid.

The compounds of formula (I) have at least one asymmetric centre and therefore exist in more than stereoisomeric form. The invention extends to each of these forms individually and to mixtures thereof, such as racemates.

The compounds of formula (I) and their salts may form solvates, such as hydrates, and there are included as part of the invention, wherever a compound of formula (I) or a salt thereof is herein referred to.

A preferred group of compounds within formula (I) is of formula (II):

(II)

wherein $R_1 1$ is nitro, cyano, $CF_3$, $C_2F_5$, $OCF_3$, methyl, ethyl, iso-propyl or acetyl; and $R_5$, $R_6$, $R_7$ and $R_8$ are as defined in formula (I).

Suitable and preferred values for the variables are as described for the corresponding variables in formula (I).

The invention further provides a process for the preparation of a compound of formula (I) which comprises reacting a compound of formula (III):

(III)

wherein Y' and $R_2$' are Y and $R_2$ respectively or moieties convertible thereto, $R_5^1$ is hydrogen or hydroxy, and the remaining variables are as defined in formula (I), with a compound of formula (IV):

(IV)

wherein L is a leaving group and E is a group —$NR_6R_7$ (wherein $R_6$ and $R_7$ are as defined in formula (I)) or a leaving group; thereafter (when E is a leaving group), converting to a group —$NR_6R_7$ by reacting with a compound $HNR_6R_7$; wherein $R_6$ and $R_7$ are as defined in formula (I); thereafter optionally converting Y' and $R_2$' to Y and $R_2$ respectively and $R_5^1$ (when hydroxy) is converted to $R_5$ (other than hydrogen); and thereafter optionally forming a pharmaceutically acceptable salt thereof.

When E is a leaving group, the intermediates of formula (IA) are novel and form an aspect of this invention.

(IA)

Suitable examples of leaving groups L and E include $C_{1-6}$ alkoxy, $C_{1-6}$ alkylthio, chloro, bromo, iodo, phenoxy, mesylate and tosylate.

The preferred leaving group is ethoxy.

The reactions are preferably carried out in an inert solvent such as a lower alkanol (e.g. ethanol), diethyl ether or acetonitrile at −10° C. to reflux, preferably at ambient temperature to 50° C.

Conversions of Y' to Y and $R_2$' to $R_2$ are conventional in the art of aromatic organic chemistry.

Compounds of formula (III) (wherein $R_5^1$ is hydroxy) are known compounds or may be prepared by methods analogous to those used for structurally similar known compounds, as disclosed in the aforementioned patent publications.

Intermediates of the formula (III) wherein J is O may be prepared from the corresponding 3,4 epoxy compounds, also described in the aforementioned patent publications, by hydrolysis with acid (cis and trans) or base (trans only).

Compounds of formula (IV) are known compounds or may be prepared by methods analogous to those used for structurally similar known compounds.

The compound of formula (Iv) wherein the groups L and E are both ethoxy is commercially available in the United Kingdom.

Intermediates of formula (III) wherein $R_5^1$ is hydrogen, J is $NR_8$ and $R_8$ is hydrogen may be prepared from intermediates of formula (V) according to the following reaction scheme:

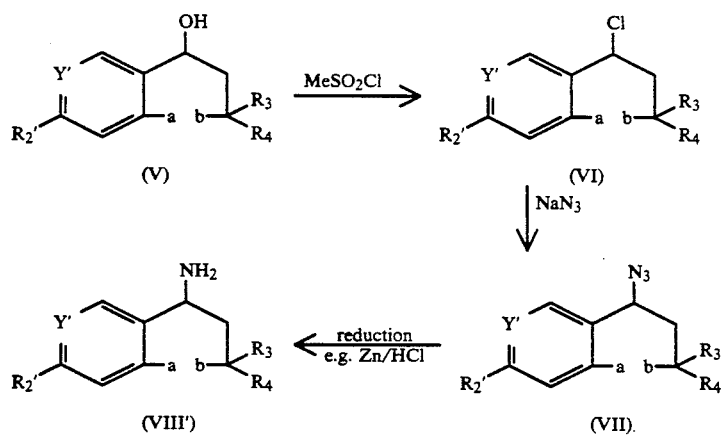

Intermediates of the formula (V) are prepared by methods given in GB 2204868A (Sandoz Limited). It should be appreciated that compounds of formula (V) are compounds of formula (III) wherein $R_5^1$ is hydrogen and J is O.

Intermediates of the formula (VIII) wherein $R_8$ is $C_{1-6}$ alkyl and $R_5$ is hydrogen may be prepared from intermediates of formula (VIII)' by conventional amine alkylation or reductive amination methods.

It will be appreciated that, when $R_5$ is hydroxy, $C_{1-6}$ alkoxy or $C_{1-7}$ acyloxy, it is preferred that the compound of formula (I) is isolated in the form of a pure single enantiomer, preferably the (3S,4R)-isomer. This may either be prepared by resolution or stereospecifically using resolved intermediates, such as described in Example 12 thereinafter.

As mentioned previously, the compounds of formula (I) have been found to have blood-pressure lowering activity. They are therefore useful in the treatment of hypertension. They are also believed to be of potential use in the treatment of other disorders hereinbefore referred to.

The present invention accordingly provides a pharmaceutical composition which comprises a compound of formula (I) or a pharmaceutically acceptable salt thereof, and a pharmaceutically acceptable carrier. In particular, the present invention provides an anti-hypertensive or bronchodilator pharmaceutical composition which comprises an effective amount of a compound of formula (I) or a pharmaceutically acceptable salt thereof, and a pharmaceutically acceptable carrier.

The present invention also provides a process for the preparation of a pharmaceutical composition which comprises admixing a compound of formula (I), or a pharmaceutically acceptable salt thereof, and a pharmaceutically acceptable carrier.

The compositions are preferably adapted for oral administration. However, they may be adapted for other modes of administration, for example parenteral administration for patients suffering from heart failure. Other alternative modes of administration include sublingual or transdermal administration. A composition may be in the form of spray, aerosol or other conventional method of inhalation, for treating respiratory tract disorders.

The compositions may be in the form of tablets, capsules, powders, granules, lozenges, suppositories, reconstitutable powders, or liquid preparations, such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling or tabletting. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The present invention further provides a method of prophylaxis or treatment of hypertension or respiratory tract disorders in mammals including man, which comprises administering to the suffering mammal an effective amount of a compound of formula (I) or a pharmaceutically acceptable salt thereof.

An effective amount will depend on the relative efficacy of the compound, the severity and nature of the disorder being treated and the weight of the sufferer. However, a unit dose form of a composition of the invention may contain from 0.05 to 500 mg of a compound of the invention and more usually from 0.1 to 50 mg, for example 0.5 to 25 mg such as 0.5, 1, 2, 5, 10, 15 or 20 mg. Such compositions may be administered from 1 to 6 times a day, more usually from 1 to 4 times a day, in a manner such that the daily dose is from 0.01 to 25 mg for a per kg body weight and more particularly from 0.1 to 10 mg/kg.

No toxicological effects are indicated at the aforementioned dosage ranges.

The compounds of formula (I) and pharmaceutically acceptable salts thereof are believed to show a synergistic effect with ACE inhibitor or β-blocker antihypertensive agents and such combination products, for concomitant or sequential administration are within the present application.

The present invention therefore provides a compound of formula (I) or a pharmaceutically acceptable salt thereof for use as an active therapeutic substance.

The invention also provides the use of a compound of formula (I) or a pharmaceutically acceptable salt thereof in the manufacture of a medicament for use in the treatment or prophylaxis of hypertension and/or respiratory tract disorders.

The present invention further provides a compound of formula (I) or a pharmaceutically acceptable salt thereof for use in the treatment or prophylaxis of hypertension and/or respiratory tract disorders.

The following descriptions and examples relate to the preparation of intermediates and compounds of formula (I):

DESCRIPTION 1

(3S,4R)-6-Cyano-3,4-dihydro-2,2-dimethyl-4-methylamino-2H-1-benzopyran-3-ol (D1)

A solution of methylamine in dry ethanol was added to a solution of (3S,4R)-6-cyano-3,4-dihydro-3,4-epoxy-2,2-dimethyl-2H-1-benzopyran* (1.0 g) in dry ethanol, and the resulting solution stirred at room temperature for 2 days. Evaporation of solvent in vacuo gave the title compound as a gum (1.0 g) which was used without further purification.

$^1$H n.m.r. (CDCl$_3$) δ 1.22 (s, 3H), 1.55 (s, 3H), 1.55–2.40 (br s, 2H), 2.34 (s, 3H), 3.61 (d, 1H), 3.70 (d, 1H), 6.88 (d, 1H), 7.43 (dd, 1H), 7.62 (d, 1H).

* GB 2204868A (Sandoz Limited)

DESCRIPTION 2 i)

(3S,4R)-6-Ethyl-4-amino-3,4-dihydro-2,2-dimethyl-2H-1-benzopyran-3-ol (+)-mandelate (+)-Mandelic acid (0.57 kg) and trans-6-ethyl-4-amino-3,4-dihydro-2,2-dimethyl-2H-1-benzopyran-3-ol** (0.75kg) were dissolved in warm 2-propanol (18 L). The solution was concentrated to 12 L and crystallised to give the title compound (0.523 kg).

$[α]_D^{20} = +56.5°$, c=1 in MeOH.

** EP-A-250077 (Beecham Group p.l.c.).

ii)

(3S,4R)-6-Ethyl-3,4-dihydro-2,2-dimethyl-3-hydroxy-4-trimethylammonium-2H-1-benzopyran iodide (3S,4R)-6-Ethyl-4-amino-3,4-dihydro-2,2-dimethyl-2H-1-benzopyran-3-ol (+)-mandelate (2.0 g) was dissolved in methylene chloride (150 mL) and sodium hydroxide solution (50 mL, 5%) added. The mixture was stirred vigorously for 1 h, then separated. The organic layer was dried and evaporated to give a colourless solid which was dissolved in DMF (20 mL) at 0° C. and sodium carbonate (2.23 g) added. Methyl iodide (1.3 mL) was then added and the reaction mixture stirred at room temperature for 3 h, after which time a further 1.3 mL of methyl iodide was added. The reaction mixture was stirred at room temperature for 96 h, then the solvents were removed in vacuo, and water (50 mL) added. The product was filtered to give the title compound as a solid (1.49 g).

iii)

(3S,4S)-6-Ethyl-3,4-dihydro-3,4-epoxy-2,2-dimethyl-2H-1-benzopyran (3S,4R)-6-Ethyl-3,4-dihydro-2,2-dimethyl-3-hydroxy-4-trimethylammonium-2H-1-benzopyran iodide (1.49 g) was suspended in dry THF (20 mL) and a suspension of potassium tert-butoxide (0.47 g) in dry THF (10 mL) added dropwise at 0° C. The reaction mixture was stirred at room temperature for 3 h, then the solvent removed in vacuo and the residue partitioned between methylene chloride and dilute sodium bicarbonate solution. The organic layer was washed with sodium bicarbonate solution, brine and then dried. Evaporation of solvent in vacuo gave the title compound as a solid (0.7 g).

$[α]_D^{20} = -13.71°$, c=0.992 in CHCl$_3$.

iv)

(3S,4R)-6-Ethyl-3,4-dihydro-2,2-dimethyl-4-methylamino-2H-1-benzopyran-3-ol

A solution of methylamine in dry ethanol was added to a solution of (3S,4S)-6-3,4-dihydro-3,4-epoxy-2,2-dimethyl-2H-1-benzopyran (0.68 g) in dry ethanol, and the resulting solution stirred at room temperature for 5 days. Evaporation of solvent in vacuo gave the title compound as a gum (0.71 g) which was used without further purification.

$^1$H n.m.r. (CDCl$_3$) δ 1.20 (t, 3H), 1.22 (s, 3H), 1.50 (s, 3H), 1.55–2.05 (br s, 2H), 2.37 (s, 3H), 2.60 (q, 2H), 3.61

(d, 1H), 3.68 (d, ¹H), 6.73 (d, ¹H), 6.98 (dd, 1H), 7.05 (d, 1H).

Prepared in a similar manner to that described above, from the corresponding epoxides described in EP-A-205292 and EP-A-376524 and methylamine in ethanol were:

trans-6-Trifluoromethyl-3,4-dihydro-2,2-dimethyl-4-methylamino-2H-1-benzopyran-3-ol (D3)

¹H n.m.r. (CDCl₃) δ 1.22 (s, 3H), 1.55 (s, 3H), 1.90–2.50 (br s, 2H), 2.37 (s, 3H), 3.63 (d, ¹H), 3.74 (d, 1H), 6.89 (d, 1H), 7.42 (dd, ¹H), 7.53 (dd, ¹H).

trans-3,4-Dihydro-2,2-dimethyl-4-methylamino-2H-pyrano-3,2-c]pyridin-3-ol (D4)

¹H n.m.r. (CDCl₃) δ 1.20 (s, 3H), 1.50 (s, 3H), 2.38 (s, 3H), 2.60–3.30 (br s, 2H), 3.55 (d, 1H), 3.78 (d, 1H), 6.65 (d, 1H), 8.15 (dd, 1H), 8.45 (d, 1H).

trans-6-Acetyl-3,4-dihydro-2,2-dimethyl-4-methylamino-2H-1-benzopyran-3-ol (D5)

¹H n.m.r. (CDCl₃) δ 1.18 (s, 3H), 1.53 (s, 3H), 2.20 (s, 3H), 2.32 (s, 3H), 3.30 (s, 2H, exchanged with D₂O), 3.62 (d, 1H), 3.70 (d, 1H), 6.80 (d, 1H), 7.52 (dd, 1H), 7.75 (d, 1H).

trans-6-Isopropyl-3,4-dihydro-2,2-dimethyl-4-methylamino-2H-1-benzopyran-3-ol (D6)

¹H n.m.r. (CDCl₃) δ 1.18 (s, 3H), 1.20 (s, 3H), 1.24 (s, 3H), 1.50 (s, 3H), 1.65–2.60 (br s, 2H), 2.38 (s, 3H), 2.86 (sept, 1H), 3.61 (d, 1H), 3.70 (d, 1H), 6.73 (d, ¹H), 7.02 (dd, ¹H), 7.08 (d, ¹H).

trans-6-Pentafluoroethyl-3,4-dihydro-2,2-dimethyl-4-methylamino-2H-1-benzopyran-3-ol (D7)

¹H n.m.r. (CDCl₃) δ 1.22(s, 3H), 1.55 (s, 3H), 1.80–2.70 (br s, 2H), 2.32 (s, 3H), 3.65 (d, 1H), 3.78 (d, 1H), 6.91 (d, 1H), 7.38 (dd, 1H), 7.50 (d, 1H).

EXAMPLE 1

Trans-N'-4-(6-Cyano-3,4-dihydro-2,2-dimethyl-2H-1-benzopyran-3-ol)]-1,2-diaminocyclobutene-3,4-dione (E1)

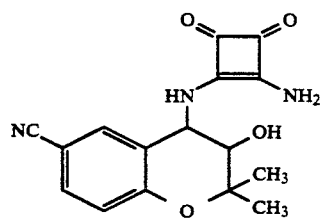

3,4-Diethoxycyclobutene-1,2-dione (commercially available from Aldrich Chemical Co.) (390 mg) was added to a solution of 6-cyano-4-amino-3,4-dihydro-2,2-dimethyl-2H-1-benzopyran-3-ol* (500 mg) in dry ethanol (15 mL) and the solution stirred at room temperature for 18 h. A saturated solution of ammonia in ethanol (4 mL) was then added, and stirring continued for 4 h. The resulting precipitate was filtered off and recrystallised from ethanol/N,N-dimethylformamide to give the title compound as a colourless solid (200 mg) having m.pt. >300° C.

¹H nmr (DMSO-d₆O δ 1.15 (s, 3H), 1.40 (s, 3H), 3.58 (dd, J=9, 6Hz, 1H), 4.80–5.10 (m, 1H), 5.96 (d, J=6Hz, 1H), 6.95 (d, J=9Hz, 1H), 7.30–7.80 (brm, 3H), 7.62 (dd, J=9, 2Hz, 1H), 7.20 (d, J=2Hz, 1H). 519

* EP-A-76075 (Beecham Group p.l.c.).

EXAMPLE 2 trans-N'-[4-(6-Cyano-3,4-dihydro-2,2-dimethyl-2H-1-benzopyran-3-ol)₁-₁-amino-2-methylaminocyclobutene-3,4-dione (E2)

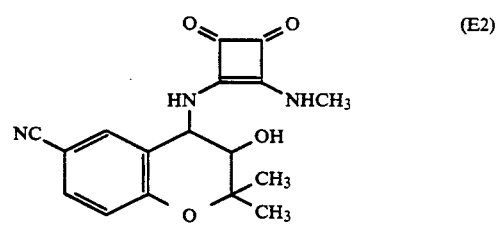

This was prepared by a method analogous to that used to prepare example 1 (E1), but using methylamine in place of ammonia.

Mpt. >300° C.

EXAMPLE 3 trans-N'-[4-(6-Cyano-3,4-dihydro-2,2-dimethyl-2H-1-benzopyran-3-ol)]-2-amino-1-methylaminocyclobutene-3,4-dione (E3)

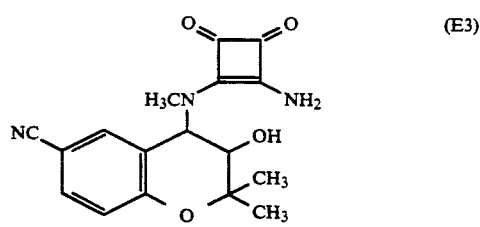

This was prepared by a method analogous to that used to prepare example 1 (E1), but using the methylaminoalcohol, in place of the aminoalcohol.

Mpt.: >300° C.

EXAMPLE 4 trans-N'-[4-(6-Trifluoromethyl-3,4-dihydro-2,2-dimethyl-2H-1-benzopyran-3-pl)]-1,2-diaminocyclobutene-3,4-dione (E4)

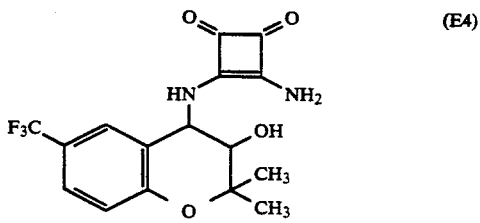

This was prepared by a method analogous to that used to prepare example 1 (E1), but using the 6-CF₃ aminoalcohol in place of the 6-cyanoaminoalcohol.

Mpt >300° C.

EXAMPLE 5 trans-N'-[4-(6-Ethyl-3,4-dihydro-2,2-dimethyl-2H-1-benzopyran-3-ol)]-1,2-diaminocyclobutene-3,4-dione (E5)

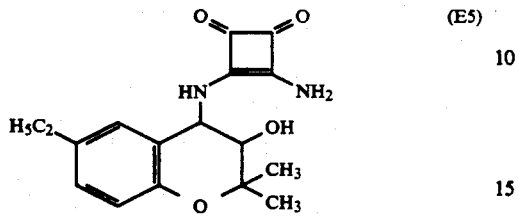

(E5)

This was prepared by a method analogous to that used to prepare example 1 (E1), but using the 6-ethyl aminoalcohol in place of the 6-cyanoaminoalcohol.

Mass spectrum: Found M+ 316.1426; $C_{17}H_{20}N_2O_4$ requires M+ 316.1423.

EXAMPLE 6 trans-N'-[4-(6-Ethyl-3,4-dihydro-2,2-dimethyl-2H-1-benzopyran-3-ol)]-2-amino-1-methylaminocyclobutene-3,4-dione (E6)

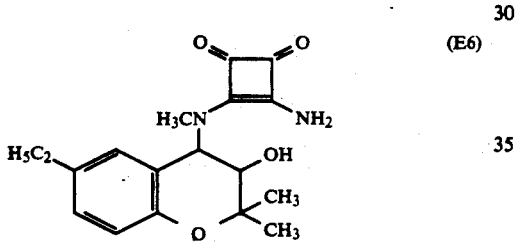

(E6)

This is prepared by a method analogous to that used to prepare example 3 (E3), but using the 6-ethylmethylaminoalcohol in place of the 6-ethylaminoalcohol.

m.pt >300° C. Found 65.11, H,6.82, N,8.36%; $C_{18}H_{22}N_2O_4$ requires C, 65.44, H,6.71, N,8.48%.

EXAMPLE 7 trans-N'-[4-(6-Trifluoromethyl-3,4-dihydro-2,2-dimethyl-2H-1-benzopyran-3-ol)]-2-amino-1-methylamino-cyclobutene-3,4-dione (E7)

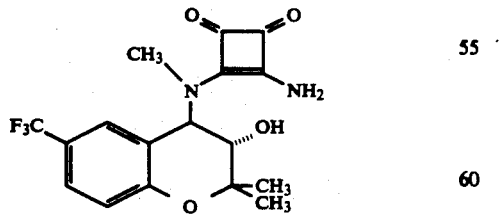

This was prepared by a method analogous to that used for example 4 (E4), but using the 6-CF3 methylamino-alcohol (D3) in place of the amino alcohol.

Anal Found C,54.78, H,4.56, N,7.05; $C_{17}H_{17}N_2O_4F_3$ requires C,55.14, H,4.63, N,7.54%.

EXAMPLE 8 trans-N'-[4-(3,4-dihydro-2,2-dimethyl-2H-pyrano[3,2-c]pyridin-3-ol)]-2-amino-1-methylamino-cyclobutene-3,4dione-(E8)

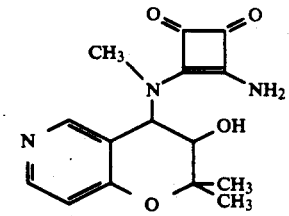

This was prepared by a method analogous to that used for example 1 (E1), but using the pyrano[3,2-c]pyridine methylaminoalcohol (D4) in place of the aminoalcohol. Mass spectrum: Found M+ 303.1219; $C_{15}H_{17}N_3O_4$ requires M+ 303.1219.

EXAMPLE 9 trans-N'-[4-(6-Cyano-3,4-dihydro-2,2-dimethyl-2H-1-benzopyran-3-ol)]-2-amino-1-ethylaminocyclobutene-3,4dione (E9)

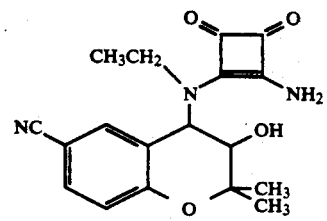

This was prepared by a method analogous to that used for example 3 (E3), but using the ethylaminoalcohol in place of the methylaminoalcohol. po Mass Spectrum: Found M+ 341.1383; $C_{18}H_{19}N_3O_4$ requires M+ 341.1376.

EXAMPLE 10 trans-N'-[4-(6-Trifluoromethylmethoxy-3,4-dihydro-2,2-dimethyl-2H-1-benzopyran-3-ol)]-1,2-diaminocyclobutene-3,4-dione (E10)

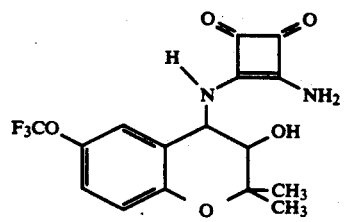

This was prepared by a method analogous to that used for example 1 (E1), but using the 6-trifluoromethylmethoxyaminoalcohol in place of the aminoalcohol.

Mass Spectrum: Found M+ 372.0927; $C_{16}H_{15}N_2O_5F_3$ requires M+ 372.0925.

EXAMPLE 11 trans-$N^1$-[4-(6-Cyano-3,4-dihydro-2,2-dimethyl-2H-1-benzopyran-3-ol)]-2-amino-1-propylaminocyclobutene-3,4-dione ($E_{11}$)

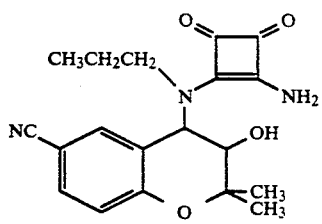

This was prepared by a method analogous to that used for example 1 (E1), but using the propylaminoalcohol in place of the aminoalcohol.

Anal. Found C,63.82, H,5.99, N,11.68% $C_{19}H_{22}N_3O_4$ requires C,64.03, H,6.22, N, 11.79%.

EXAMPLE 12 trans-(3S,4R)-$N^1$-[4-(6-Ethyl-3,4-dihydro-2,2-dimethyl-2H-1-benzopyran-3-ol)]-2-amino-1-methylaminocyclobutene-3,4-dione (E12)

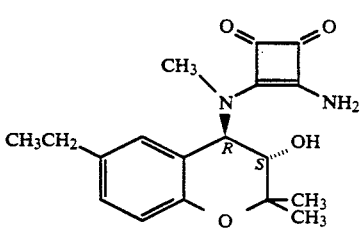

This was prepared by a method analogous to that used for example 6 (E6), but using the (3S,4R)-methylamino alcohol (D2) in place of the racemic methylaminoalcohol.

Mass Spectrum: Found M+ 330.1565; $C_{18}H_{22}N_2O_4$ requires M+ 330.1579

$[\alpha]_D^{20} = -38.2°$ c=0.953 in DMSO.

EXAMPLE 13 trans-$N^1$-[4-]6-Cyano-3,4-dihydro-2,2-dimethyl-2H-1-benzopyran-3-ol)]-1,2-dimethylaminocyclobutene-3,4-dione dione (E13)

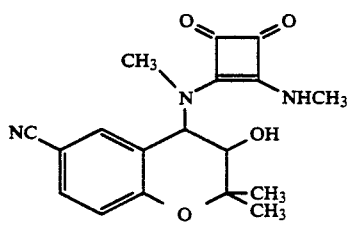

This was prepared by a method analogous to that used for example 2 (E2), but using the methylaminoalcohol in place of the aminoalcohol.

Mass Spectrum: Found M+ 341.1379; $C_{18}H_{19}N_3O_4$ requires M+ 341.1376.

EXAMPLE 14 trans-$N^1$-[4-(6-Acetyl-3,4-dihydro-2,2-dimethyl-2H-1-benzopyran-3-ol)]-2-amino-1-methylaminocyclobutene-3,4-dione (E14)

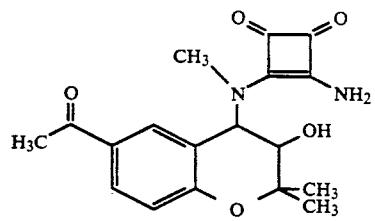

This was prepared by a method analogous to that used for example 1 (E1), but using the 6-acetylmethylaminoalcohol (D5) in place of the aminoalcohol.

Mass Spectrum: Found M+ 344.1378; $C_{18}H_{20}N_2O_5$ requires M+ 344.1386.

EXAMPLE 15 trans-$N^1$-[4-(6-Cyano-3,4-dihydro-2,2-dimethyl-2H-1-benzopyran)]-1,2-diaminocyclobutene-3,4-dione (E15)

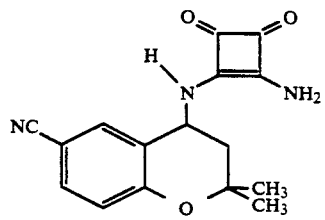

This was prepared by a method analogous to that used for example 1 (E1), but using 6-cyano-4-amino-3,4-dihydro-2,2-dimethyl-2H-1-benzopyran (prepared as described in EP-A-359537 Beecham Group p.l.c.) in place of the amino alcohol.

$^1$H n.m.r. (DMSO-$d_6$O $\delta$ 1.30 (s, 3H), 1.43 (s, 3H), 1.89 (dd, 1H), 2.28 (dd, 1H), 5.20 (m, 1H), 6.95 (d, 1H), 7.25–7.95 (br s, 3H), 7.64 (dd, 1H), 7.74 (d, 1H).

Anal. Found C,64.36, H,5.10, N,13.95%; $C_{16}H_{15}N_3O_3$ requires C,64.64, H,5.09, N,14.13%.

EXAMPLE 16 trans-$N^1$-[4-(6-Isopropyl-3,4-dihydro-2,2-dimethyl-2H-1-benzopyran-3-ol)-2-amino-1-methylaminocyclobutene-3,4-dione (E16)

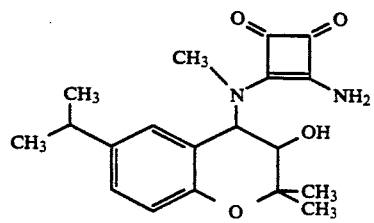

This was prepared by a method analogous to that used for example 1 (E1), but using the 6-isopropyl methylaminoalcohol (D6) in place of the aminoalcohol.

Mass Spectrum Found M+ 344.1741; $C_{19}H_{24}N_2O_4$ requires M+ 344.1736.

EXAMPLE 17

(3S,4R)-N¹-[4-(6-Cyano-3,4-dihydro-2,2-dimethyl-2H-1-benzopyran-3-ol)]-2-amino-1-methylaminocyclobutene-3,4-dione (E17)

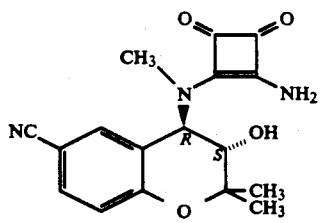

This was prepared by a method analogous to that used for example 3 (E3), but using the (3S,4R) methylaminoalcohol (D1) in place of the racemic methylaminoalcohol.

m.pt. >300° C.; $[\alpha]_D^{20} = -54.50° = 0.6$ in DMSO.

EXAMPLE 18 trans-N¹-[4-(6-Pentafluoroethyl-3,4-dihydro-2,2-dimethyl-2H-1-benzopyran-3-ol)]-2-amino-1-methylaminocyclobutene-3,4-dione (E18)

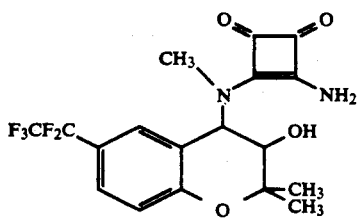

This was prepared by a method analogous to that used for example 1 (E1), but using the 6-pentafluoroethylmethylaminoalcohol (D7) in place of the aminoalcohol.

Mass Spectrum: Found M+ 420.1117; $C_{18}H_{17}N_2O_4F_5$ requires M+ 420.1111.

PHARMACOLOGICAL DATA

1. Antihypertensive Activity

Systolic blood pressures were recorded by a modification of the tail cuff method described by I. M. Claxton, M. G. Palfreyman, R. H. Poyser, R. L. Whiting, European Journal of Pharmacology, 37, 179 (1976). A W+W BP recorder, model 8005 was used to display pulses. Prior to all measurements rats were placed in a heated environment (33.5°±0.5° C.) before transfer to a restraining cage. Each determination of blood pressure was the mean of at least 5 readings. Spontaneously hypertensive rats (ages 12-18 weeks) with systolic blood pressures >180 mmHg were considered hypertensive.

Example 1 lowers blood pressure by 50% at a dose of 3 mg/kg p.o.

Example 2 lowers blood pressure by 17% at a dose of 3 mg/kg p.o.

Example 3 lowers blood pressure by 58% at a dose of 3 mg/kg p.o.

Example 12 lowers blood pressure by 24% at a dose of 0.05 mg/Kg p.o.

2. Bronchodilator Activity

Male guinea pigs (300–600 g) were stunned by a blow to the head and bled from the carotid artery. The trachea was exposed, dissected free of connective tissue, and transferred to oxygenated Krebs solution at 37° C. Next, spirals (2 per trachea) were prepared by cutting the whole trachea spirally along its longitudinal axis and then dividing this spiral lengthwise. Each preparation was mounted, using silk thread, in a 10 ml organ bath filled with Krebs solution at 37° C. and bubbled with 5% $CO_2$ with $O_2$. The resting tension of the preparations was set at 2 g and changes in muscle tension were monitored isometrically by means of a UFI (2 oz) force and displacement transducer (Ormed Ltd) connected to a Linseis pen recorder. All preparations were allowed to equilibrate for 60 minutes. During this equilibration period the preparations were washed by upward displacement at 15 minute intervals and, if necessary, the resting tension was readjusted to 2 g using a mechanical micromanipulator system.

Once a steady resting tension had been obtained, the preparations were dosed simultaneously with the test compound ($10^{-8} - 2 \times 10^{-5}$M), and finally a maximum relaxation achieved by addition of $10^{-3}$M isoprenaline. The fall in tension evoked by the test compound was expressed as a percentage of the total relaxation evoked in the presence of $10^3$ isoprenaline. Appropriate concentration-relaxation curves were then constructed and values for potency ($IC_{50}$) were obtained.

[The composition of Krebs solution is: sodium chloride 118.07 mM, sodium hydrogen carbonate 26.19 mM, potassium chloride 4.68 mM, potassium orthophosphate 1.18 mM, magnesium sulphate septahydrate 1.8 mM and calcium chloride 2.52 mM;pH ca. 7.45.]

| Example | Results Inhibition of spontaneous tone in guinea-pig isolated trachealis $IC_{50}$. |
|---|---|
| E1 | $3.7 \times 10^{-6}$ M |
| E2 | $4.0 \times 10^{-6}$ M |
| E3 | $3.1 \times 10^{-6}$ M |

We claim:

1. A compound of formula (I) or a pharmaceutically acceptable salt thereof:

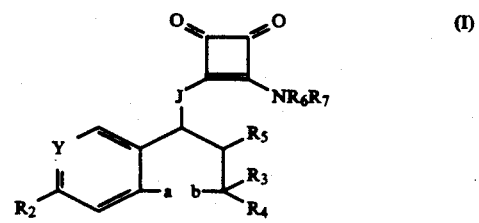

wherein
a and b together form an —O— or —CH₂— linkage or a bond;
Y is C—R₁
wherein
either one of R₁ and R₂ is hydrogen and the other is nitro, cyano, halo, —CF₃, C₂F₅, formyl, aldoxime, CF₃O, NO₂—CH=CH—, NC—CH=CH—; or
R$_x$X— wherein R$_x$ is C₁ to C₆ alkyl, phenyl or furyl said phenyl or furyl each being optionally substituted by one, two or three of $C_1$ to $C_4$ alkyl, $C_1$ to $C_4$ alkoxy, nitro, halo, $CF_3$ and cyano; and X is $C=O$, $O.C=O$, $C=O.O$, CHOH, SO, $SO_2$, O.SO, $O.SO_2$, CONH, O.CONH, $CO-CH=CH$, $C=NHOH$, $C=NNH_2$; or $R_yR_zNH$—, wherein $R_y$ and $R_z$ are independently hydrogen or $C_1$ to $C_6$ alkyl and Z is $C=O$, SO or $SO_2$; or $(R_wO)_2P(O)W$, wherein $R_w$ is hydrogen or $C_1$ to $C_6$ alkyl and W is O or a bond; or $R_1$ is a $C_3$ to $C_8$ cycloalkyl group or a $C_1$ to $C_6$ alkyl optionally substituted by $R_9$ which is hydrogen, $C_1$ to $C_6$ alkoxy, amino optionally substituted by one or two $C_1$ to $C_6$ alkyl, $C_1$ to $C_7$ alkanoylamino, $C_3$ to $C_8$ cycloalkyloxy or $C_3$ to $C_8$ cycloalkylamino and $R_2$ is hydrogen; or one of $R_1$ and $R_2$ is nitro, cyano or $C_1$ to $C_3$ alkylcarbonyl and the other is a nitro, cyano, halo, $C_1$ to $C_3$ alkylcarbonyl, methoxy or amino optionally substituted by one or two $C_1$ to $C_6$ alkyl or by $C_2$ to $C_7$ alkanoyl; or either one of $R_3$ and $R_4$ is hydrogen or $C_1$ to $C_4$ alkyl and the other is $C_1$ to $C_4$ alkyl; or $R_3$ and $R_4$ togehter are $C_2$ to $C_5$ polymethylene;

$R_5$ is hydrogen, hydroxy, $C_1$ to $C_6$ alkoxy or $C_1$ to $C_7$ acyloxy or $ONO_2$;

$R_6$ and $R_7$ are independently hydrogen, $C_1$ to $C_6$ alkyl; or (when $R_6$ is hydrogen), then $R_7$ is allyl, propargyl or $C_3$ to $C_6$ cycloalkyl;

J is O or $NR_8$ wherein $R_8$ is hydrogen or $C_1$ to $C_6$ alkyl.

2. A compound according to claim 1 wherein Y is $C-R_1$ where $R_1$ is nitro, cyano, $CF_3$, $C_2F_5$, $OCF_3$, methyl, ethyl, iso-propyl or cetyl and $R_2$ is hydrogen.

3. A compound according to claim 1 wherein $R_3$ and $R_4$ are both methyl.

4. A compound according to claim 1 wherein $R_5$ is hydroxy or hydrogen.

5. A compound according to claim 1 wherein $R_6$ and $R_7$ are hydrogen.

6. A compound according to claim 1 wherein J is $NR_8$, where $R_8$ is as defined in claim 1.

7. A compound according to claim 1 wherein $R_5$ is as defined in claim 1 (other than hydrogen) and the cyclobutene moiety is trans- to the $R_5$ group.

8. A compound selected from the list consisting of;
trans-N'-[4-(6-Cyano-3,4-dihydro-2,2-dimethyl-2H-1-benzopyran-3-ol)]-1,2-diaminocyclobutene-3,4dione,
trans-N'-[4-(6-Cyano-3,4-dihydro-2,2-dimethyl-2H-1-benzopyran-3-ol)]-1-amino-2-methylaminocyclobutene-3,4-dione,
trans-N'-[4-(6-Cyano-3,4-dihydro-2,2-dimethyl-2H-1-benzopyran-3-ol)]-2-amino-1-methylaminocyclobutene-3,4-dione,
trans-N'-[4-(6-Trifluoromethyl-3,4-dihydro-2,2-dimethyl-2H-1-benzopyran-3-ol)]-1,2-diaminocyclobutene-3,4-dione,
trans-N'-[4-(6-Ethyl-3,4-dihydro-2,2-dimethyl-2H-1-benzopyran-3-ol)]-1,2-diaminocyclobutene-3,4dione,
trans-N'-[4-(6-Ethyl-3,4-dihydro-2,2-dimethyl-2H-benzopyran-3-ol)]-2-amino-1-methylaminocyclobutene-3,4-dione,
trans-N'-[4-(6-Trifluoromethyl-3,4-dihydro-2,2-dimethyl-2H-1-benzopyran-3-ol)]-2-amino-1-methycyclobutene-3,4-dione,
trans-N'-[4-(3,4-Dihydro-2,2-dimethyl-2H-pyrano-[3,2-c]pyridin-3-ol)]-2-amino-1-methylaminocyclobutene-3,4-dione,
trans-N'-[4-(6-Cyano-3,4-dihydro-2,2-dimethyl-2H-1-benzopyran-3-ol)]-2-amino-1-ethylaminocyclobutene-3,4-dione,
trans-N'-[4-(6-Trifluoromethylmethoxy-3,4-dihydro-2,2-dimethyl-2H-1-benzopyran-3-ol)]-1,2-diaminocyclobutene-3,4-dione,
trans-$N^1$-[4-(6-Cyano-3,4-dihydro-2,2-dimethyl-2H-1-benzopyran-3-ol)]-2-amino-1-propylaminocyclobutene-3,4-dione,
trans-(3S,4R)-$N^1$-[4-(6-Ethyl-3,4-dihydro-2,2-dimethyl-2H-1-benzopyran-3-ol)]-2-amino-1-methylaminocyclo-butene-3,4-dione,
trans-$N^1$-[4-(6-Cyano-3,4-dihydro-2,2-dimethyl2H-1-benzopyran-3-ol)]-1,2-dimethylaminocyclobutene-3,4-dione,
trans-$N^1$-[4-(6-Acetyl-3,4-dihydro-2,2-dimethyl-2H-1-benzopyran-3-ol)]-2-amino-1-methylaminocyclobutene-3,4-dione,
trans-$N^1$-[4-(6-Cyano-3,4-dihydro-2,2-dimethyl-2H-1-benzopyran)]-1,2-diaminocyclobutene-3,4-dione,
trans-$N^1$-[4-(6-Isopropyl-3,4-dihydro-2,2-dimethyl-H-1-benzopyran-3-ol)-2-amino-1-methylaminocyclobutene-3,4-dione,
(3S,4R)-$N^1$-[4-(6-Cyano-3,4-dihydro-2,2-dimethyl-2H-1-benzopyran-3-ol)]-2-amino-1-methylaminocyclobutene-3,4-dione and
trans-$N^1$-[4-(6-Pentafluoroethyl-3,4-dihydro-2,2-dimethyl-2H-1-benzopyran-3-ol)]-2-amino-1-methylaminocyclobutene-3,4-dione.

9. A compound of formula (IA):

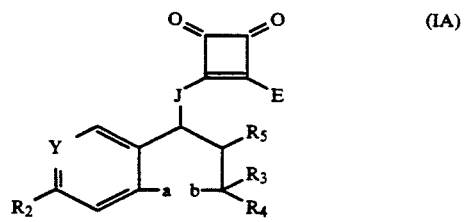

wherein E is a leaving group and the other variables are as defined in claim 1.

10. A pharmaceutical composition useful in the treatment of hypertension comprising an anti-hypertensively effective amount of a compound according to claim 1, and a pharmaceutically acceptable carrier.

* * * * *